(12) United States Patent
Dreyfuss

(10) Patent No.: US 10,548,587 B2
(45) Date of Patent: Feb. 4, 2020

(54) SUTURE ANCHOR ASSEMBLY AND METHOD OF PASSING SAME SUTURE MULTIPLE TIMES

(71) Applicant: Arthrex, Inc., Naples, FL (US)

(72) Inventor: Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 315 days.

(21) Appl. No.: 15/359,070

(22) Filed: Nov. 22, 2016

(65) Prior Publication Data

US 2018/0140291 A1    May 24, 2018

(51) Int. Cl.
*A61B 17/04* (2006.01)

(52) U.S. Cl.
CPC .. *A61B 17/0401* (2013.01); *A61B 2017/0403* (2013.01); *A61B 2017/0414* (2013.01)

(58) Field of Classification Search
CPC ........ A61B 17/0401; A61B 2017/0496; A61B 2017/0412; A61B 2017/0414; A61B 2017/0403; A61B 2017/0404; A61B 2017/0406; A61B 2017/0409; A61B 2017/0416; A61F 2002/0888; A61F 2/0811
See application file for complete search history.

(56) References Cited

U.S. PATENT DOCUMENTS

| | | | | |
|---|---|---|---|---|
| 5,520,702 | A * | 5/1996 | Sauer | A61B 17/0469 29/751 |
| 2012/0283749 | A1 * | 11/2012 | Sauer | A61B 17/0401 606/144 |
| 2013/0144338 | A1 | 6/2013 | Stone et al. | |
| 2013/0345749 | A1 | 12/2013 | Sullivan et al. | |
| 2014/0039551 | A1 * | 2/2014 | Donahue | A61B 17/0401 606/232 |
| 2015/0173739 | A1 | 6/2015 | Rodriguez et al. | |

FOREIGN PATENT DOCUMENTS

| | | | |
|---|---|---|---|
| EP | 2 774 545 A2 | 9/2014 | |
| WO | WO 2014/022838 A1 | 2/2014 | |
| WO | WO 2016/160068 A2 | 10/2016 | |

* cited by examiner

*Primary Examiner* — Erich G Herbermann
(74) *Attorney, Agent, or Firm* — Blank Rome LLP

(57) ABSTRACT

A suture anchor assembly and method of tissue repair using the same suture of the suture anchor assembly. The suture anchor assembly has a fixation device, at least one repair suture coupled to a portion of the fixation device, and a shuttle loop coupled to the portion of the fixation device. The repair suture has a passing end configured to pass through tissue and a free end opposite the passing end. The shuttle loop has at least one linking region, such as an eyelet configured to receive the passing end of the at least one suture repair.

10 Claims, 4 Drawing Sheets

SUTURE ANCHOR ASSEMBLY AND METHOD OF PASSING SAME SUTURE MULTIPLE TIMES

FIELD OF THE INVENTION

The present invention relates to a suture anchor assembly for tissue repair and method of passing the same suture of that suture anchor assembly multiple times to ease suture management and evenly apply tension forces on the repair.

BACKGROUND OF THE INVENTION

Conventional methods of tissue repair often require multiple sutures where each suture must be individually tied to complete the repair. This complicates the repair and also makes management of so many sutures difficult. Therefore, a need exists for a method of suture repair that reduces the number of sutures and knots while also providing the appropriate tension needed for the repair and to avoid damage to the suture and/or tissue.

SUMMARY OF THE INVENTION

Accordingly, the present invention provides a suture anchor assembly that comprises a fixation device, at least one repair suture coupled to a portion of the fixation device, and a shuttle loop coupled to the portion of the fixation device. The repair suture has a passing end configured to pass through tissue and a free end opposite the passing end. The shuttle loop has at least one linking region configured to receive the passing end of the at least one suture repair. In a preferred embodiment, the linking region is an eyelet.

The present invention may also provide a method of tissue repair that uses the same repair suture, comprising the steps of loading the repair suture on a fixation device, the repair suture having a passing end and an opposite free end; loading a shuttle loop on the fixation device; installing the pre-loaded fixation device in bone; passing the passing end of the repair suture through or around tissue; linking the passing end of the repair suture to a linking region of the shuttle loop; and passing the linking region of the shuttle loop and the passing end of the repair suture through at least a portion of the fixation device by rotating the shuttle loop, thereby forming at least one tissue fixation loop in the repair suture. In a preferred embodiment, these passing steps are repeated to form multiple tissue fixation loops in the repair suture.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing figures.

DETAILED DESCRIPTION OF THE PREFERRED EMBODIMENTS

Referring to FIGS. 1, 2a-2e, and 3, the present invention generally relates to a suture anchor assembly 100 and method of using the same for tissue repair. The present invention facilitates suture management during the repair, particularly by passing the same suture of the assembly multiple times through or around the tissue and through the anchor placed in bone. Additionally, because the same suture is used, only one knot is required to complete the repair and tension is evenly distributed on the suture and the tissue.

Figure 1:
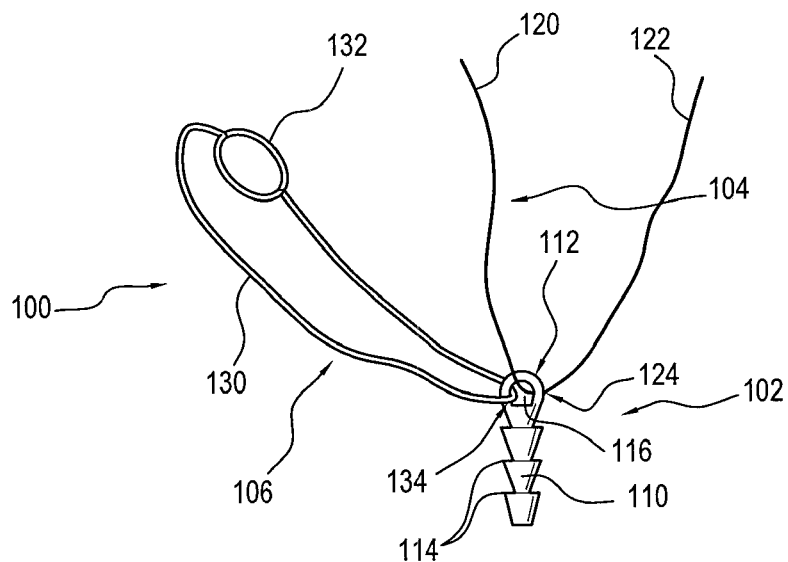
FIG. 1 is an elevational view of a suture anchor assembly according to an exemplary embodiment of the present invention.

As seen in FIG. 1, suture anchor assembly 100 generally includes a fixation device 102 with a repair suture 104 and a shuttle loop 106 coupled thereto. The fixation device 102 may be any known anchor configured for installation in bone. In a preferred embodiment, fixation device 102 includes an anchor body 110 that includes outer ridges 114 for gripping the bone hole and a portion 112 for coupling repair suture 104 and shuttle loop 106 thereto. The portion 112 of fixation device 102 may be, for example, an eyelet portion located at an end of anchor body 110 that has an opening 116 configured to allow repair suture 104 and shuttle loop 106 to pass therethrough.

Repair suture 104 may be a flexible strand that includes a passing end 120 and an opposite free end 122. Passing end 120 is configured to pass through or around tissue 90 (FIGS. 2a-2e) while free end 122 remains free. A portion 124 between passing and free ends 120 and 122 engages fixation device 102, such as by extending portion 124 through opening 116 of the eyelet portion 112 of fixation device 102.

Shuttle loop 106 includes a closed loop body 130 and a linking region 132 for linking to the passing end 120 of repair suture 104, as seen in FIGS. 2A-2D. A portion 134 of closed loop body 130 engages fixation device 102, such as by extending portion 134 through the eyelet portion 112 of fixation device 102. Linking region 132 is preferably an eyelet formed in closed loop body 130. To form eyelet 132 in closed loop body 130, eyelet 132 may be spliced or may be formed from a bifurcating braider. Shuttle loop 106 preferably has a fixed diameter and may be formed of any flexible material, such a polyester braid and the like. The eyelet is sized to allow the passing end 120 of repair suture 104 to easily pass therethrough. Alternatively, the linking region 132 may be another type of linking mechanism, such as a splice in closed loop body 130 through which the passing end 120 of repair suture 104 may be threaded or a doubled over suture.

Figure 2A:
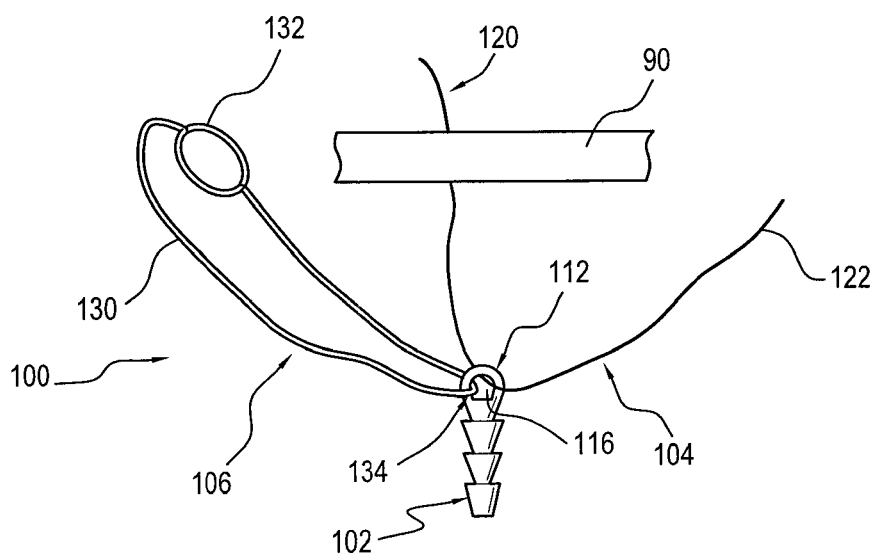
FIGS. 2a-2e are schematic elevational views showing the sequence of steps of a method of tissue repair in accordance with an exemplary embodiment of the present invention, using the suture anchor assembly illustrated in FIG. 1.
Figure 2B:
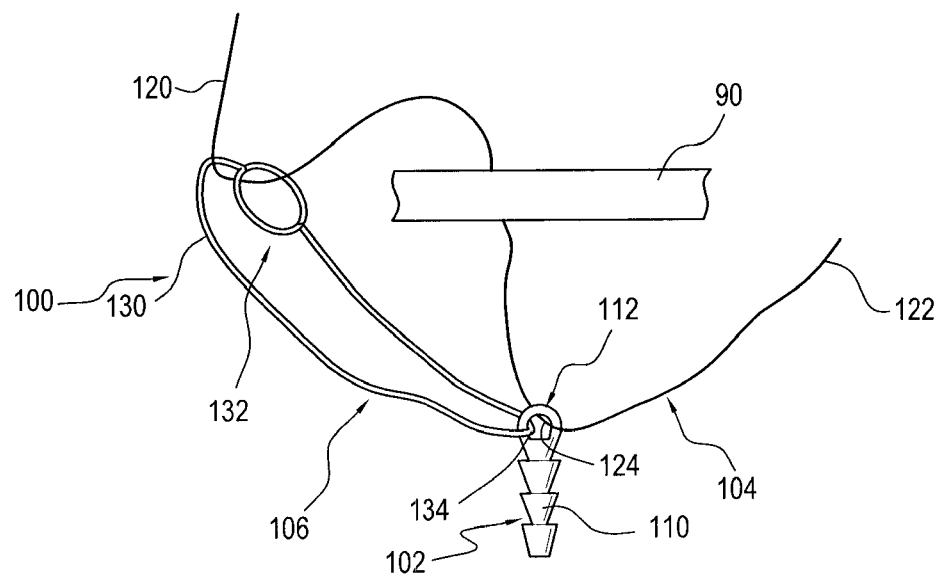
Figure 2C:
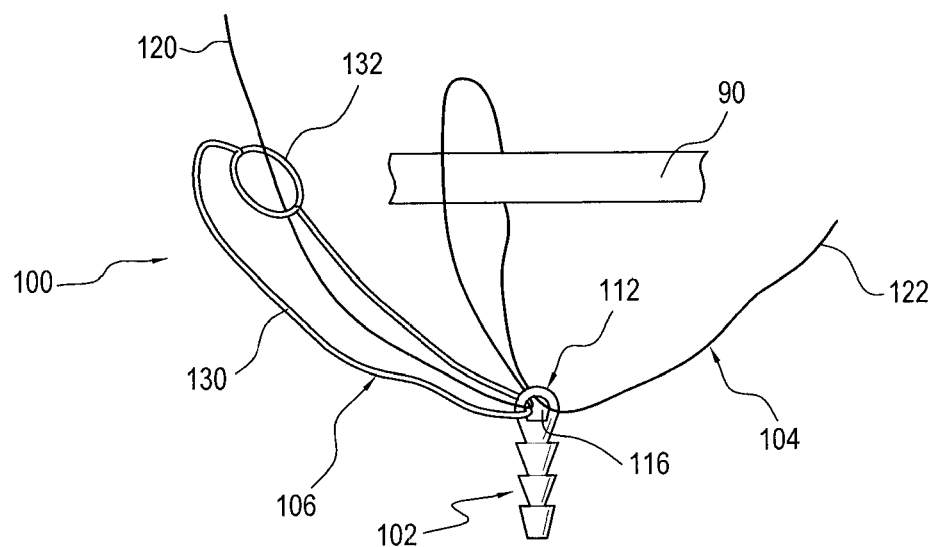
Figure 2D:
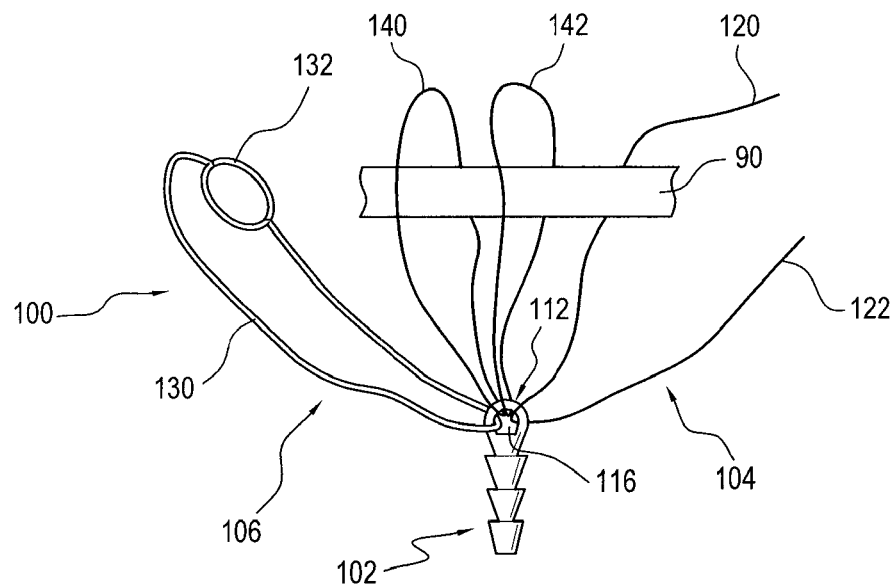

A method of tissue repair in accordance with an exemplary embodiment of the present invention using the suture anchor assembly 100 generally comprises the steps of loading the repair suture 104 on the fixation device 102; loading the shuttle loop 106 on the fixation device 102; installing the loaded fixation device in the bone hole; passing the passing end 120 of the repair suture 104 through or around tissue 90 (FIG. 2a); linking the passing end 120 of the repair suture 104 to linking region 132 of shuttle loop 106 (FIG. 2b); and passing the linking region 132 of shuttle loop 106 and passing end 120 of repair suture 104 through a portion of fixation device 102, such as eyelet portion 112, by rotating shuttle loop 106, thereby forming at least one tissue fixation loop 140 in repair suture 104 (FIG. 2c).

To load repair suture 104 on fixation device 102, repair suture 104 may be passed through a portion of fixation device 102, such as its eyelet portion 112, such that the portion 124 of repair suture 102 between its ends is received in opening 116 of eyelet portion 112, as seen in FIG. 1. To load shuttle loop 106 on fixation device 102, the flexible material of loop body 130 is first passed through a portion of fixation device 102, such as its eyelet portion 112, and then attached to itself, such as be splicing, to form the fixed diameter loop body 130. As such, portion 134 of loop body 130 is received in opening 116 of eyelet portion 112. Shuttle loop 106 is preferably loaded separately from repair suture 104. The loaded fixation device 102 may then be installed in a bone hole in any conventional manner.

To link the passing end 120 of repair suture 104 to linking region 132 of shuttle loop 106, the passing end 120 may be extended through the eyelet of linking region 132, as seen in FIG. 2*b*, or alternatively through a splice in loop body 130 of shuttle loop 106. Free end 122 of repair suture 104 remains free and unused during these steps the tissue repair. Once linked together, the passing end 120 and the linking region 132 may be passed through the opening 116 of eyelet portion 112 of fixation device by rotating shuttle loop 106, thereby forming the at least one tissue fixation loop 140, as seen in FIG. 2*c*.

The above steps may be repeated a select number of times to form additional tissue fixation loops using the same repair suture 104. That is, once one tissue fixation loop 140 is created, another tissue fixation loop 142 (FIG. 2*d*) may be created in repair suture 104 by removing the passing end 120 from linking region 132; again passing the passing end 120 of repair suture 104 through or around tissue 90; linking the passing end 120 to linking region 132 of shuttle loop 106; and rotating shuttle loop 106 to pull the linked passing end 120 of repair suture 104 and linking region 132 of shuttle loop 106 through the eyelet portion 112 of fixation device 102. These passing steps may again be repeated to form a third tissue fixation loop 144. Although, three tissue fixation loops 140, 142 and 144 are shown, any number of fixation loops may be created using the method of the present invention.

Figure 2E:
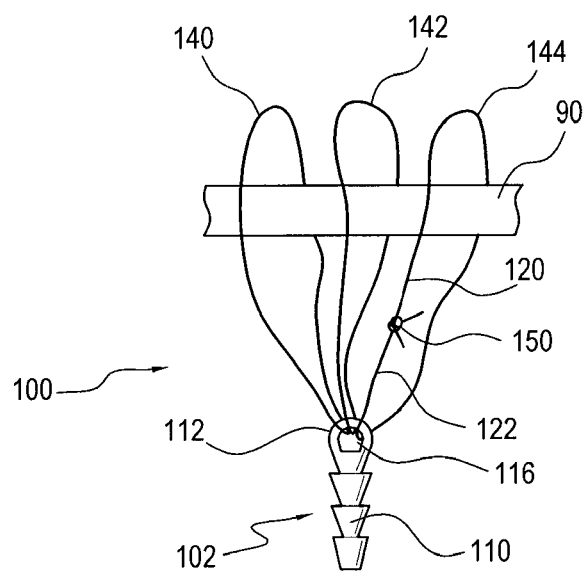

Once the final tissue fixation loop, such as tissue fixation loop 144, of repair suture 104 is formed, free end 122 of repair suture 104 may be tied to passing end 120 to form a knot 150, as seen in FIG. 2*e*, and complete the tissue repair. Thus only one knot 150 is need to complete the tissue repair, thereby simplifying the repair. The shuttle loop 106 may be cut and removed from the fixation device 102. Prior to tying knot 150, one or both of the passing and free ends 120 and 122 may be tensioned to approximate tissue 90 to the bone. Because tissue fixation loops 140, 142, and 144 are all part of repair suture 104, the forces on repair suture 104 are evenly distributed when tensioned. This even distribution of tension avoids a high load being placed on one suture or suture loop, which could cause the suture to fail or tear through the tissue.

Figure 3:
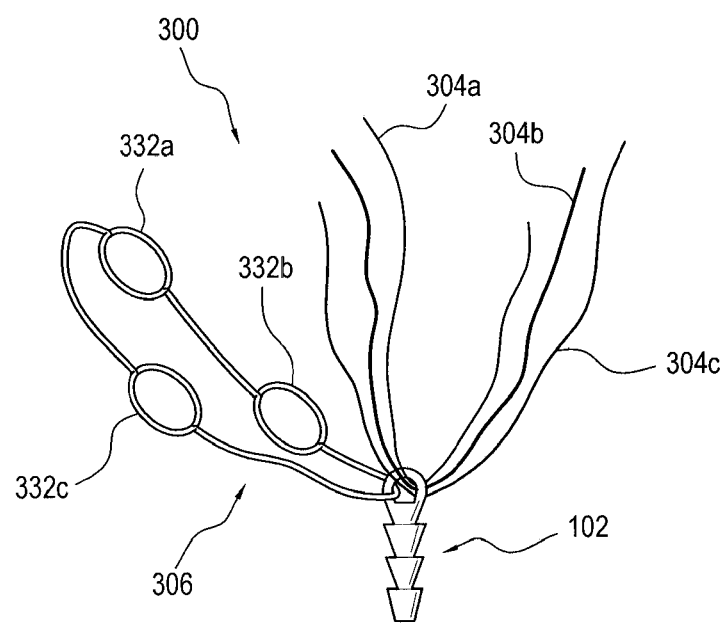
FIG. 3 is an elevational view of a suture anchor assembly according to an alternative exemplary embodiment of the present invention.

FIG. 3 illustrates an alternative embodiment of the suture anchor assembly of the present invention. Suture anchor assembly 300 of FIG. 3 is similar to suture anchor assembly 100 except that fixation device 102 is loaded with a plurality of repair sutures, such as repair sutures 304*a*, 304*b*, and 304*c*, and the shuttle loop 306 includes a plurality of linking regions, such as linking regions 332*a*, 332*b*, and 332*c*. In one embodiment, the number of linking regions corresponds to the number of repair sutures. Although three repair sutures and three linking regions are shown, any number of repair sutures and any number of linking regions may be used.

Suture anchor assembly 300 may be used in the same manner as discussed above for tissue repair. That is, the passing ends 320*a*, 320*b*, and 320*c* may be passed through or around tissue and linked to corresponding linking regions 332*a*, 332*b*, and 332*c* of shuttle loop 306. Once linked, shuttle loop 306 may be rotated to pass the linking regions 332*a*, 332*b*, and 332*c* and passing ends 320*a*, 320*b*, and 320*c* through a portion of fixation device 102, such as eyelet portion 112, such that each repair suture 320*a*, 320*b*, and 320*c* forms at least one tissue fixation loop. Those passing steps may then be repeated to form additional tissue fixation loops in each of repair sutures 320*a*, 320*b*, and 320*c*.

While particular embodiments have been chosen to illustrate the invention, it will be understood by those skilled in the art that various changes and modifications can be made therein without departing from the scope of the invention as defined in the appended claims.

What is claimed is:

1. A suture anchor assembly, comprising: a fixation device; at least one repair suture coupled to a portion of the fixation device, the at least one repair suture having a passing end configured to pass through tissue and a free end opposite the passing end; and a shuttle loop coupled to the portion of the fixation device, the shuttle loop being formed of a length of flexible material comprising a closed loop body and having at least one linking region formed in the closed loop body along the length of the flexible material, wherein the at least one linking region comprises an eyelet for receiving the passing end of the at least one repair suture.

2. A The suture anchor assembly according to claim 1, further comprising a plurality of repair sutures each having a passing end and a free end; and the shuttle loop having a plurality of linking regions, each of the plurality of linking regions being configured to receive the passing end of one of the plurality of repair sutures.

3. The suture anchor assembly according to claim 1, wherein
   the portion of the fixation device includes an eyelet portion; and
   the at least one repair suture and the shuttle loop extend through the eyelet portion.

4. The suture anchor assembly according to claim 1, wherein
   the shuttle loop is separate from the at least one repair suture.

5. The suture anchor assembly according to claim 1, wherein
   the at least one repair suture includes at least one tissue fixation loop coupled to the fixation device.

6. The suture anchor assembly according to claim 1, wherein
   the at least one repair suture includes a plurality of tissue fixation loops, each of the plurality of tissue fixation loops is coupled to the fixation device.

7. The suture anchor assembly according to claim 6, wherein
   only one of the plurality of tissue fixation loops includes a knot, the knot being formed by tying the passing and free ends of the at least one repair suture together.

8. A suture anchor assembly, comprising: a preloaded fixation device, the preloaded fixation device being preloaded with at least one repair suture and a shuttle loop, the at least one repair suture being coupled to a portion of the preloaded fixation device and having a passing end configured to pass through tissue and a free end opposite the passing end, and the shuttle loop being coupled to the portion of the preloaded fixation device, the shuttle loop comprising a closed loop body that has at least one linking region formed in the closed loop body, the linking region comprising an eyelet for receiving the passing end of the at least one repair suture.

9. The suture anchor assembly according to claim 8, wherein
   the shuttle loop is formed of a length of flexible material and the at least one linking region is formed along the length of flexible material.

10. The suture anchor assembly according to claim 8, wherein
    the passing end and the free end of the at least one repair suture are tied together.

* * * * *